United States Patent [19]

Cornellier

[11] Patent Number: 5,401,263
[45] Date of Patent: * Mar. 28, 1995

[54] FEMININE URINARY AID PACKAGE

[76] Inventor: Maurice H. Cornellier, P.O. Box 2123, Inverness, Fla. 34451

[ * ] Notice: The portion of the term of this patent subsequent to Jul. 19, 2011 has been disclaimed.

[21] Appl. No.: 255,182

[22] Filed: Jun. 7, 1994

Related U.S. Application Data

[63] Continuation-in-part of Ser. No. 100,265, Aug. 2, 1993, Pat. No. 5,330,453.

[51] Int. Cl.⁶ ............................................. A61F 5/44
[52] U.S. Cl. .................................. 604/329; 4/144.2; 222/527
[58] Field of Search ............... 604/329; 4/144.1, 144.2, 4/451; 222/526, 527; 141/297, 331, 337

[56] References Cited

U.S. PATENT DOCUMENTS

| | | |
|---|---|---|
| D. 208,609 | 9/1967 | Garland . |
| 2,734,198 | 2/1956 | Kutsche . |
| 2,878,486 | 3/1959 | Bartlett et al. . |
| 3,535,714 | 10/1970 | Bjork ................................. 4/144.2 |
| 3,572,318 | 3/1971 | Garland . |
| 3,613,123 | 10/1971 | Langstrom . |
| 3,731,869 | 5/1973 | Griffin . |
| 3,964,111 | 6/1976 | Packer . |
| 4,023,216 | 5/1977 | Li . |
| 4,108,222 | 8/1978 | Kaufman . |
| 4,528,703 | 7/1985 | Kraus . |
| 4,605,403 | 8/1986 | Tucker ............................... 604/385.1 |
| 4,681,573 | 7/1987 | McGovern et al. . |
| 4,734,941 | 4/1988 | DeWitt et al. . |
| 4,751,751 | 6/1988 | Reno . |
| 4,815,151 | 3/1989 | Ball . |
| 4,937,890 | 7/1990 | Tafur . |
| 5,091,998 | 3/1992 | Irazabal . |
| 5,261,531 | 11/1993 | Nieves ................................. 206/205 |
| 5,330,453 | 7/1994 | Cornellier ........................... 604/329 |

*Primary Examiner*—Randy C. Shay
*Attorney, Agent, or Firm*—Barnes, Kisselle, Raisch, Choate, Whittemore & Hulbert

[57] ABSTRACT

A feminine urinary aid package that includes a closed flat enclosure, preferably of tearable paper composition, that is constructed to be opened by a user, and a feminine urinary aid disposed within such enclosure and removable therefrom when the enclosure is opened. The urinary aid includes a one-piece body of water resistant biodegradable water soluble composition having a pair of flat side portions with elongated parallel linear side edges. The side portions are integrally joined to each other along contiguous side edges, and a triangular end portion is integrally joined to the side portions at end edges of the side portions that are perpendicular to the side edges. Preferably, creases extend along at least the end edges of the flat side portions where joined to the end portion, and along the side edges where joined to each other. The aid is folded flat along the creases when disposed within the package, and is openable by a user when removed from the package to impart an open V-shaped cross section to the body as viewed in a direction parallel to the side edges.

7 Claims, 1 Drawing Sheet

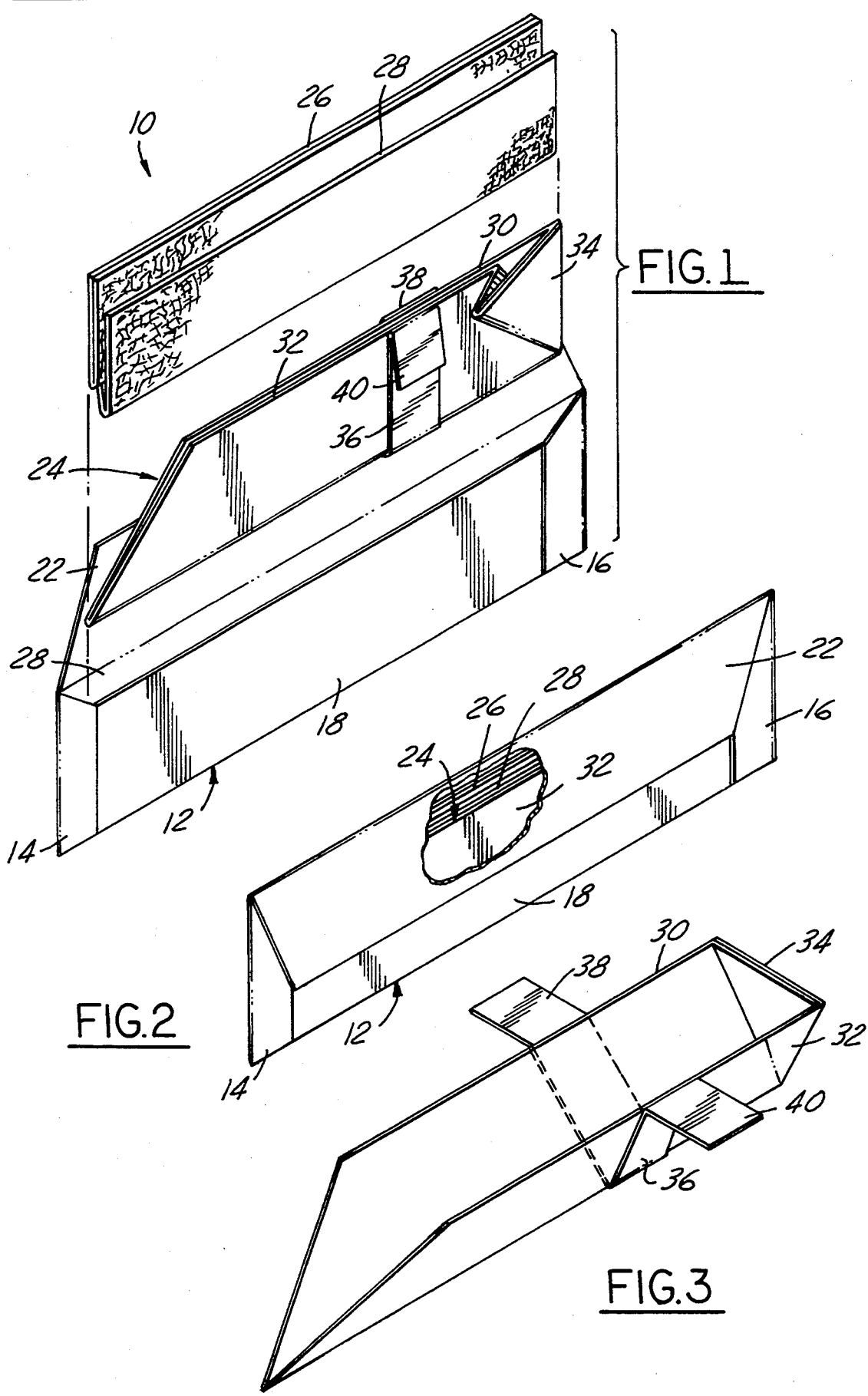

FEMININE URINARY AID PACKAGE

This application is a continuation-in-part of application Ser. No. 08/100,265, filed Aug. 2, 1993, now U.S. Pat. No. 5,330,453.

The present invention is directed to devices for assisting human females to urinate when sanitary facilities are unavailable, and more particularly to a device for assisting a human female to urinate in a standing position.

BACKGROUND AND SUMMARY OF THE INVENTION

There are many instances in which sanitary facilities for female urination are unavailable in the sense of being either unsanitary, overcrowded or completely lacking. For example, at public events such as concerts or sporting events, the facilities provided often have less than desired cleanliness or availability. When camping or hiking, for example, facilities are often completely lacking. It is a principal object of the present invention to provide a device that will aid or assist a human female to urinate while standing. It is a more specific object of the present invention to provide a feminine urinary aid package that may be readily sold in quantity in a box or individually in a dispensing machine, and is particularly well suited for transport in a purse, back-pack or the like.

A feminine urinary aid package in accordance with the present invention includes a closed flat enclosure, preferably of tearable paper composition, that is constructed to be opened by a user, and a feminine urinary aid disposed within such enclosure and removable therefrom when the enclosure is opened. The urinary aid includes a one-piece body of water resistant biodegradable water soluble composition having a pair of flat side portions with elongated parallel linear side edges. The side portions are integrally joined to each other along contiguous side edges, and a triangular end portion is integrally joined to the side portions at end edges of the side portions that are perpendicular to the side edges. Preferably, creases extend along at least the end edges of the flat side portions where joined to the end portion, and along the side edges where joined to each other. The aid is folded flat along the creases when disposed within the package, and is openable by a user when removed from the package to impart an open V-shaped cross section to the body as viewed in a direction parallel to the side edges.

The aid in the preferred embodiment of the invention has an open second end spaced from the one end and defined by second end edges angulated away from the end portions toward the contiguous side edges. The aid preferably also includes a handle integrally extending from at least one of the side portions, with a crease being formed along the handle so that the handle is foldable against the side portion along the crease when the aid is disposed within the flat package. Preferably, at least one tissue of water absorbent construction is disposed within and removable from the package along with the urinary aid.

BRIEF DESCRIPTION OF THE DRAWINGS

The invention, together with additional objects, features and advantages thereof, will be best understood from the following description, the appended claims and the accompanying drawing in which:

FIG. 1 is an exploded perspective view of a feminine urinary aid package in accordance with a presently preferred embodiment of the invention;

FIG. 2 is a perspective view, partially sectioned, of the aid package illustrated in FIG. 1; and FIG. 3 is a perspective view of the aid removed from the package of FIGS. 1 and 2 and unfolded for use.

DETAILED DESCRIPTION OF PREFERRED EMBODIMENT

The disclosure of parent application Ser. No. 08/100,265, filed Aug. 2, 1993 is incorporated herein by reference.

FIGS. 1-3 illustrate a feminine urinary aid package 10 in accordance with a presently preferred embodiment of the invention as comprising a flat rectangular enclosure 12 in the form of an envelope of tearable or severable sheet paper composition. End flaps 14,16 are folded over a short side flap 18, and a second side flap 20 has a closure flap 22 projecting therefrom with gum or other adhesive suitable for closing the envelope enclosure. A feminine urinary aid 24 is removably disposed within envelope enclosure 12, as are a pair of water absorbent tissues 26,28.

As shown in FIGS. 1 and 3, aid 24 comprises a one-piece body having integrally joined side sections or portions 30,32 and one double-thickness end portion or section 34. Side portions 30,32 each comprise a section of biodegradable cellulose (paper) composition having spaced parallel upper and lower side edges, with the lower edges being integrally joined to each other. End section 34 is integrally joined to side sections 30,32 along the end edges of the side sections to close one end of body 24. Body 24 is creased along the contiguous and integrally joined lower side edges of side sections 30,32, along the contiguous and integrally joined end edges of side sections 24,26 where joined to end section 30, and at an angle along side section 32 as shown in FIG. 1. In this way, body 24 may be folded into a flat geometry as illustrated in FIG. 1 for removable receipt within envelope 12, and may be unfolded when removed from envelope 12 to impart an open generally V-shaped cross section to the aid body. The end of the body remote from end section 34 is open, with the parallel end edges of side sections 30,32 being angulated away from end portion 34 in the direction of the joined contiguous side edges. Aid 24 is preferably formed of a single sheet that overlaps at end 34.

A length of sheet cellulose (paper) composition 36 extends around side sections 30,32, and has a pair of free ends 38,40 that project outwardly from side sections 30,32. Ends 38,40 are creased at the junctures with the respective side sections so as to be foldable thereagainst (FIG. 1) when body 24 is disposed within envelope 12, and to extend therefrom (FIG. 3) when the body is unfolded so as to form a pair of tabs or flaps that function as handles during use. When body 24 is removed from envelope package 12 and unfolded to the configuration of FIG. 3, the body thus forms a funnel-like construction that is closed at one end and open at the other. The closed end of the device is placed by hand beneath the urethra so that, in use, the stream of urine is directed in an uninterrupted flow along the length of the device and away from the user's body. After use of aid body 24 and tissues 26,28, the same may be refolded and reinserted into envelope package 12 for proper disposal.

I claim:

1. A feminine urinary aid package that comprises:

a closed flat enclosure constructed to be opened by a user, and a feminine urinary aid disposed within said enclosure and removable from said enclosure when said enclosure is opened, said aid comprising a one-piece body of water resistant biodegradable water soluble composition having a pair of flat side portions each with elongated parallel linear side edges and one end edge perpendicular to said side edges, said side portions being integrally joined to each other along contiguous side edges of said portions, and a triangular end portion integrally joined to said side portions at said end edges so as to close one end of said body and impart an open-topped V-shaped cross section to said body viewed in a direction parallel to said side edges.

2. The aid package set forth in claim 1 further comprising creases extending along at least said end edges of said flat side portions where joined to said end portion and along said side edges where joined to each other, said aid being folded flat along said creases when disposed within said package and unfoldable when removed from said package to impart said open-topped V-shaped cross section to said aid.

3. The aid package set forth in claim 2 wherein said body has an open second end spaced from said one end.

4. The aid package set forth in claim 3 further comprising a handle integrally extending from at least one of said side portions, and a crease along said handle with said handle being folded against said side portion along said crease when said aid is disposed in said package.

5. The aid package set forth in claim 3 wherein said side portions of said body each have a second end edge remote from said one end edge, said second end edges being angulated away from said end portion toward said contiguous side edges.

6. The aid package set forth in claim 2 wherein said enclosure comprises a flat rectangular envelope of paper composition.

7. The aid package set forth in claim 6 further comprising at least one tissue of water absorbent construction disposed within and removable from said enclosure.

* * * * *